United States Patent [19]

Ricciardelli

[11] Patent Number: 4,713,095
[45] Date of Patent: Dec. 15, 1987

[54] LIQUID SEPARATOR FOR GAS ANALYZER

[75] Inventor: Robert H. Ricciardelli, Waukesha, Wis.

[73] Assignee: Criticare Systems, Inc., Milwaukee, Wis.

[21] Appl. No.: 919,894

[22] Filed: Oct. 16, 1986

[51] Int. Cl.$^4$ .............................................. B01D 19/00
[52] U.S. Cl. ........................................ 55/189; 55/204; 55/270; 128/719; 128/730
[58] Field of Search ................. 55/159, 189, 190, 203, 55/204, 270; 128/719, 730

[56] References Cited

U.S. PATENT DOCUMENTS

| 2,118,908 | 5/1938 | Vermillion | 55/203 X |
| 3,854,905 | 12/1974 | Balzer et al. | 55/159 |
| 4,099,939 | 7/1978 | Vancheri et al. | 55/270 X |
| 4,304,578 | 12/1981 | Hakala et al. | 55/189 |
| 4,461,183 | 7/1984 | Wedding | 55/270 X |
| 4,483,697 | 11/1984 | Deysson et al. | 55/204 X |
| 4,579,568 | 4/1986 | Ricciardelli et al. | 55/189 |

FOREIGN PATENT DOCUMENTS

| 2105926 | 10/1971 | Fed. Rep. of Germany | 55/204 |
| 660692 | 5/1979 | U.S.S.R. | 55/190 |

Primary Examiner—Robert Spitzer
Attorney, Agent, or Firm—Willian Brinks Olds Hofer Gilson & Lione Ltd.

[57] ABSTRACT

A gas/liquid separator for a gas analyzer includes a separation chamber having a spherically domed upper wall and a pyramid-shaped lower wall. An incoming sample to be separated is introduced into the separation chamber at one corner of the pyramid via an inlet port, liquid is removed via a liquid outlet port at the apex of the pyramid, and gas is removed via a gas outlet port in the domed upper wall. The pyramid forms internal corners, some of which converge smoothly toward the liquid outlet port so as to channel liquid away from the gas outlet port. All internal corners are separated from the gas outlet port by more than 0.05 inches in order to reduce any tendency of liquid which was collected in the internal corners to bridge across to the gas outlet port.

25 Claims, 9 Drawing Figures

LIQUID SEPARATOR FOR GAS ANALYZER

BACKGROUND OF THE INVENTION

The present invention relates to microseparators of the type used to separate gas from liquid in gas analyzers such as blood gas analyzers. In this specification the term "micro-separator" is used to designate a separator having a separator chamber with a volume less than 1 milliliter.

It is well known in the art to use a gas/liquid separator to remove liquids from air exhaled by a subject prior to supplying the exhaled air to a gas analyzer. My previous U.S. Pat. No. 4,579,568 and Hakala U.S. Pat. No. 4,304,578 describe several prior art approaches to such gas/liquid micro-separators. In the Hakala design the gas outlet for the separation chamber 5a is positioned at the internal corner formed between the components 4 and 7. This internal corner tends to direct water droplets toward the gas outlet port. Of course, any water droplets reaching the gas outlet port result in the passage of water out of the separation chamber 5a along with the desired gas sample.

SUMMARY OF THE INVENTION

The present invention is directed to an improved micro-separator for a gas analyzer, which provides improved separation characteristics for a given volume of the separation chamber.

Typically, the operation of micro-separators is governed largely by surface tension and capillary action effects, and the momentum effects which are important to the operation of larger scale separators are less significant. Such surface tension and capillary action effects make it extremely important to arrange internal corners in the separation chamber so as to draw liquid away from the gas outlet port and toward the liquid outlet port of the separation chamber. This is because liquid tends to accumulate in such internal corners.

According to this invention, a liquid separator for a gas analyzer comprises a separation chamber comprising an upper zone and a lower zone. Inlet means introduce a gas/liquid mixture into the separation chamber, gas outlet means remove gas from the upper zone, and liquid outlet means remove liquid from the lower zone. The upper zone is bounded upwardly by an upper surface which surrounds the gas outlet means, and the lower zone is bounded downwardly by a lower surface which surrounds the liquid outlet means. The upper surface is concavely shaped to drain liquid away from the gas outlet means into the lower zone, and the lower surface defines a plurality of faces which define internal corners therebetween, wherein the internal corners converge toward the liquid outlet means to draw liquid by capillary action away from the upper zone toward the liquid outlet means. The separation chamber has a volume less than 1 milliliter. Important advantages are obtained if the gas outlet means is separated from the closest one of the internal corners by a distance greater than 0.05 inches, and if the internal corners define included angles no greater than 60°.

In the preferred embodiment the upper surface is dome-shaped and the lower surface is shaped as an inverted pyramid. This shape for the separation chamber utilizes capillary forces to obtain excellent separation. Because the gas outlet means is separated from the internal corners by a distance greater than 0.05 inches, droplets accumulating in the internal corners are maintained at an adequate distance from the gas outlet means. Similarly, because the internal corners of the lower surface define a small included angle and converge toward the liquid outlet means, capillary forces draw droplets toward the liquid outlet means and away from the gas outlet means. In this way, efficient separation is provided in a small volume separation chamber.

The invention itself, together with further objects and attendant advantages, will best be understood by reference to the following detailed description, taken in conjunction with the accompanying drawings.

DETAILED DESCRIPTION OF THE PRESENTLY PREFERRED EMBODIMENTS

Figure 1:
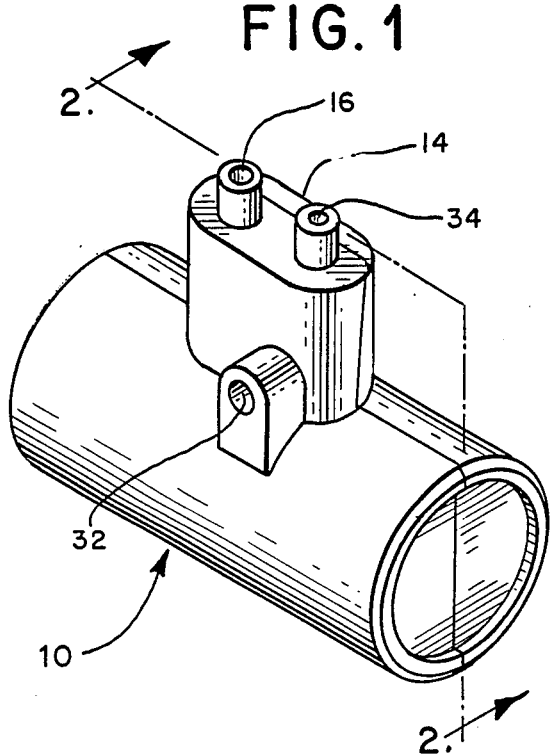
FIG. 1 is a perspective view of a separator which incorporates a presently preferred embodiment of this invention.
Figure 4:
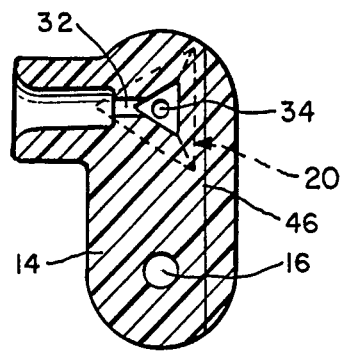
FIG. 4 is a cross-sectional view taken along line 4—4 of FIG. 2.
Figure 5:
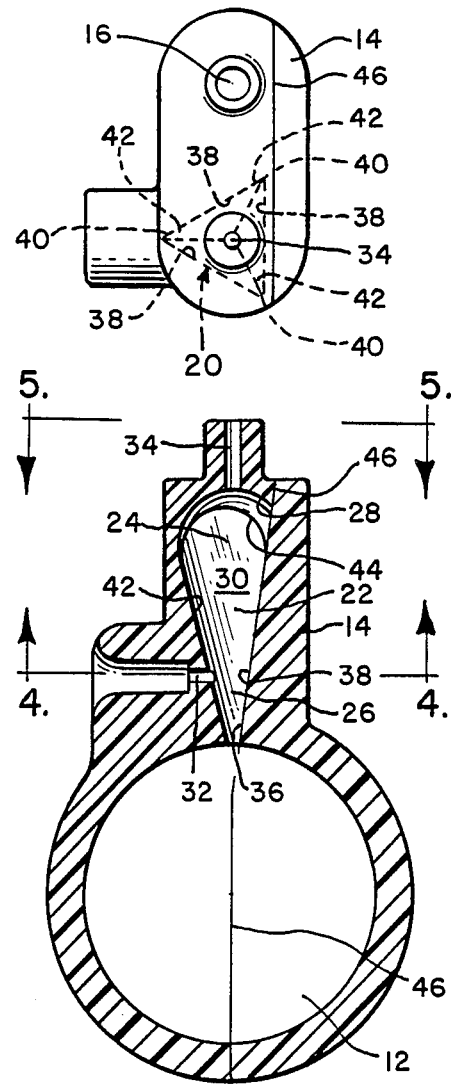
FIG. 5 is a top view of the separator of FIG. 1.
Figures 2, 3:
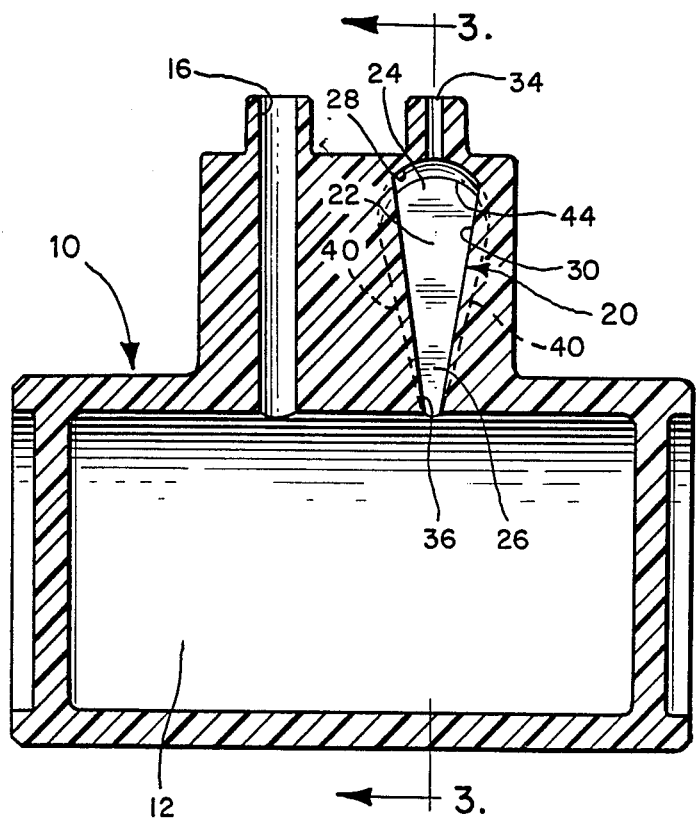
FIG. 2 is a longitudinal sectional view taken along line 2—2 of FIG. 1.
FIG. 3 is a cross-sectional view taken along line 3—3 of FIG. 2.

Turning now to the drawings, FIGS. 1 through 5 show various views of a first preferred embodiment of the separator of this invention. As shown in FIGS. 1 and 2, this embodiment includes a container 10 which incorporates a reservoir 12 that is generally cylindrical in shape. One portion of the cylindrical side wall of the container 10 defines an upstanding boss 14. This boss 14 defines a vacuum port 16 which is in fluid communication with the reservoir 12.

The boss 14 also defines a separator 20 which includes a separator chamber 22. The separator chamber 22 comprises an upper zone 24 which is generally dome-shaped and a lower zone 26 which generally has the shape of an inverted pyramid. As best shown in FIG. 2, the separator chamber 22 is generally shaped as an inverted pyramid having its base convexly shaped as a dome. The upper zone 24 is bounded by an upper surface 28 which in this embodiment is spherically concave and is shaped to shed and drain liquid into the lower zone 26. The lower zone 26 is surrounded by a lower surface 30.

Access to the separation chamber 22 is provided by three ports. A gas/liquid inlet port 32 passes through the side portion of the boss 14 into the lower zone 26. A liquid outlet port 36 connects the separation chamber 22 with the reservoir 12 and is situated at the apex of the inverted pyramid formed by the lower zone 26. A gas outlet port 34 is centered in the upper surface 28, directly aligned with the liquid outlet port 36.

In this embodiment the three faces 38 of the lower surface 30 are planar and equal in area. The three faces 38 meet at rectilinear edges 40 which are arranged tangentially to the spherical upper surface 28, and which merge smoothly with the liquid outlet port 36. Three internal corners 42 are defined at the intersections between the faces 38. These internal corners 42 converge towards the apex and the liquid outlet port 36. In addition, three arcuately shaped internal corners 44 are defined between the faces 38 and the upper surface 28.

The separator 20 has been arranged to utilize surface tension effects to provide efficient separation of liquid from gas. A gas/liquid mixture is introduced via the inlet port 32 into the lower zone 26 of the separation chamber 22 at one of the internal corners 42. Surface tension effects cause droplets in the incoming gas/liquid mixture to tend to collect in the internal corners 42 and to drain down the internal corners 42 through the liquid outlet port 36 into the reservoir 12. In this embodiment the separation between the closest one of the internal corners 42,44 and the gas outlet port 34 is approximately 0.06 inches. In general, it is important to insure that none of the internal corners 42 approaches the gas outlet port 34 by a distance less than 0.05 inches. In this way droplets which collect in the internal corners 42,44 are maintained at a sufficient distance from the gas outlet port 34 to retard movement of such droplets into the gas outlet port 34.

The container 10 with the separator 20 is well suited for use with gas analyzers such as those described in the above-identified Hakala and Ricciardelli patents. The structure and operation of such gas analyzers do not form part of this invention and therefore will not be described in detail. Here, it is sufficient to state that vacuum is applied to the vacuum port 16, an incoming sample is presented to the separator 20 via the inlet port 32, and gases to be analyzed are withdrawn from the separator via the gas outlet port 34.

In use, liquids are removed from the incoming sample by the geometrical configuration of the separator 20. In particular, the domed upper surface 28 makes it difficult for water droplets adhering to the surfaces of the separator chamber 22 to approach the gas outlet port 34 sufficiently closely to be withdrawn. The tangent intersections between the edges 40 and the upper surface 28 reduce any tendency of droplets to collect at these intersections. The internal corners 42 formed by the lower surface 30 tend to collect droplets and to channel the movement of collected droplets downwardly through the liquid outlet port 36 into the reservoir 12. In this way, liquid is separated from the incoming sample.

It should be noted that in the separator 20 the surface 28, 30 are configured to take advantage of surface tension effects. It has been found that the surprisingly simple expedient of maintaining an adequate distance between the internal corners 42,44 and the gas outlet port 34 in combination with converging internal corners 42 of the lower surface 30 provides a separator which is relatively simple to fabricate and which provides unusually good saturator efficiency. The use of internal corners which define an included angle of 60° or less further enhances efficiency.

Figure 6:
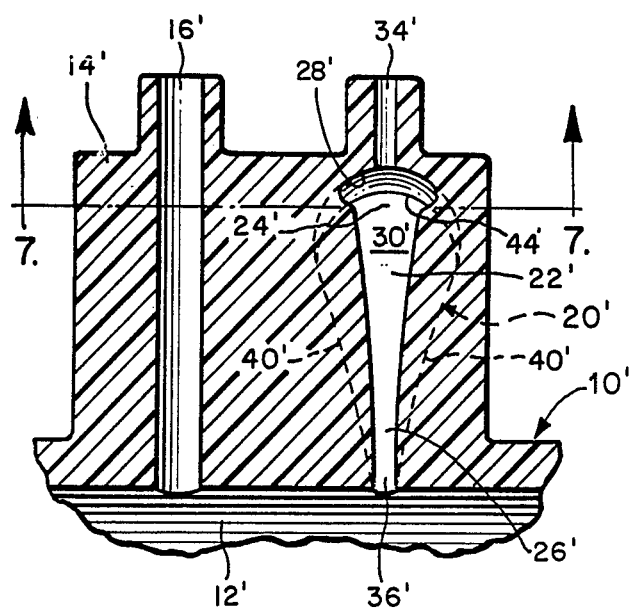
FIG. 6 is a longitudinal sectional view of a second preferred embodiment of the separator of this invention.
Figure 7:
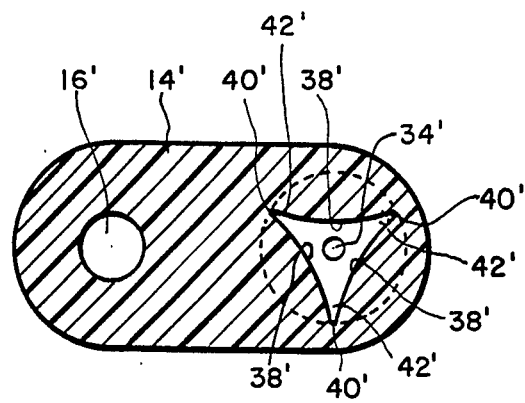
FIG. 7 is a cross-sectional view taken along line 7—7 of FIG. 6.

FIGS. 6 and 7 show two views of a second preferred embodiment of this invention in which similar elements have been designated with the same reference numerals as those used in FIGS. 1 through 5, with an added prime. The second embodiment differs from the first in that the faces 38' of the lower surface 30' are not planar but are rather convexly shaped to bow inwardly into the lower zone 26'. Similarly, the edges 40' are not rectilinear but are also bowed convexly inwardly into the lower zone 26'. By shaping the faces 38' and the edges 40' in this manner the internal corners 42' are made more acute than the internal corners 42 of the first embodiment. In this way, the surface tension effects described above are enhanced.

Figure 9:
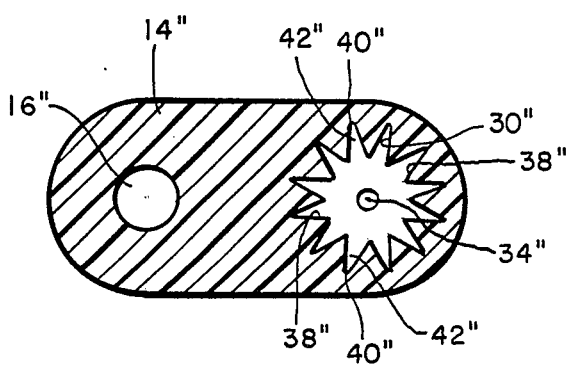
FIG. 9 is a cross sectional view taken along line 9—9 of FIG. 8.
Figure 8:
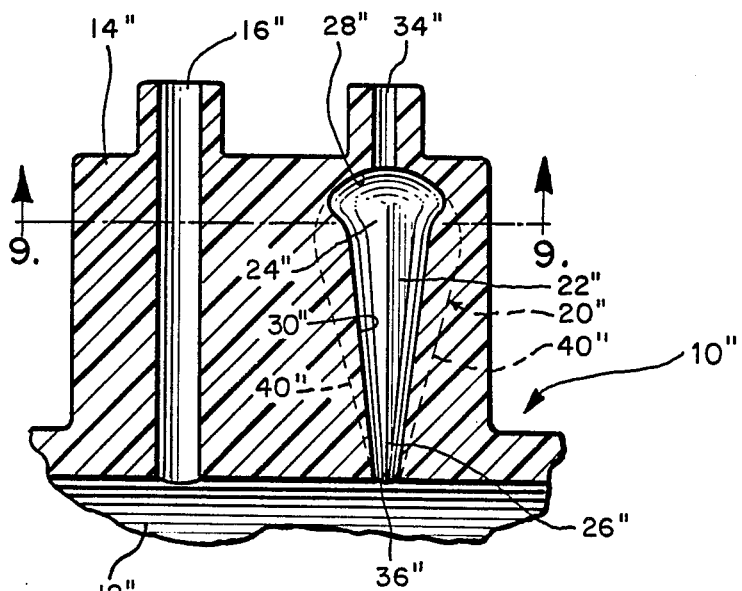
FIG. 8 is a longitudinal sectional view of a third preferred embodiment of the separator of this invention.

FIGS. 8 and 9 relate to a third preferred embodiment which further increases the number of acute internal corners which converge toward the liquid outlet port. As before, similar elements have been designated with the same reference numerals as those used in FIGS. 1–5, with an added double prime.

As shown in FIGS. 8 and 9, this third embodiment includes a boss 14" which defines a separator 20" which includes a separator chamber 22". The separator chamber 22" comprises an upper zone 24" which is generally dome shaped and a lower zone 26" which generally has the shape of a splined faceted cone. The upper zone 24" is bounded by an upper surface 28" which is spherically concave and the lower zone 26" is surrounded by a lower surface 30". As used herein, the term "pyramid" is intended in its broad sense to encompass the shape of all three of the lower zones 26, 26', 26", and variants thereof.

As before, a gas/liquid inlet port (not shown) passes through the side portion of the boss 14" into the lower zone 26", a liquid outlet port 36" connects the separation chamber 22" with a reservoir 12", and a gas outlet port 34" is centered in the upper surface 28".

The configuration of the lower surface 30" provides a large number of faces 38" which meet at edges 40" that converge toward the liquid outlet port 36" and merge tangentially with the spherical upper surface 28". In this embodiment, the faces 38" define 12 internal corners 42", each of which defines an included angle of 30°. Preferably, the gas outlet port is separated from the nearest internal corner by at least 0.05 inches, and the volume of the chamber 22" is about 96 microliters.

The third embodiment of FIGS. 8–9 differs from the embodiment of FIGS. 1–5 in that it defines a larger number of internal corners which converge toward the liquid outlet port 36", and that the internal corners 42" are more acute and therefore even more effective in directing water droplets toward the liquid outlet port 36".

The following details of construction are provided merely to define the preferred embodiments of this invention in greater detail. It should be clearly understood that these details are in no way intended to be limiting. In these embodiments the volume of the separation chamber 22 is 96 microliters and the volume of the reservoir 12 is 6 milliliters. The radius of curvature of the domed upper surface 28 is 0.128 inches, and the height of the pyramid formed by the lower surface 30 (as measured between the center of curvature of the domed upper surface 28 and the apex) is 0.444 inches. The container 10 is preferably formed of a transparent polycarbonate plastic material, preferably from two injection molded pieces which are ultrasonically welded together. Preferably, all mold lines are positioned to avoid the domed upper surface 28 in order to avoid surface irregularities, internal corners or the like which may collect adhering droplets near the gas outlet port 34. Reference numeral 46 designates one preferred location for the mold line in FIGS. 3–5.

Of course, it should be understood that a wide range of changes and modifications can be made to the preferred embodiments described above. For example, it is well within the scope of this invention to substitute a four-sided pyramid for the three-sided pyramid shown. In addition, in alternate embodiments it may be preferable to fair the upper surface 28 into the lower surface to eliminate the internal corners 44. Furthermore, the terms upper, lower and the like in the specification and the following claims have been used only for ease of reference, and are not intended to define the precise spatial orientation of the claimed invention.

It is therefore intended that the foregoing detailed description be regarded as illustrative rather than limiting, and that it be understood that it is the following claims, including all equivalents, which are intended to define the scope of this invention.

I claim:

1. A liquid separator for a gas analyzer, said separator comprising:
    means for defining a separation chamber comprising an upper zone and a lower zone;
    inlet means for introducing a gas/liquid mixture into the separation chamber;
    gas outlet means for removing gas from the upper zone; and
    liquid outlet means for removing liquid from the lower zone;
    said upper zone bounded upwardly by an upper surface which surrounds the gas outlet means;
    said lower zone bounded downwardly by a lower surface which surrounds the liquid outlet means;
    said upper surface concavely shaped to drain liquid away from the gas outlet means into the lower zone;
    said lower surface defining a plurality of facets which define a plurality of internal corners, wherein at least a portion of the internal corners converge toward the liquid outlet means to draw liquid by capillary action away from the upper zone toward the liquid outlet means;
    said gas outlet means separated from the closest one of the internal corners by a distance greater than 0.05 inches, said separation chamber having a volume less than 1 milliliter.

2. The invention of claim 1 wherein the upper surface is spherically concave.

3. The invention of claim 2 wherein the facets of the lower surface define a pyramid having an apex, and wherein the liquid outlet means is located at the apex.

4. The invention of claim 3 wherein the facets define edges at their lines of intersection, and wherein the edges are tangent to the spherically concave upper surface.

5. The invention of claim 3 wherein the plurality of facets comprises three equal area facets.

6. The invention of claim 3 wherein the facets are convexly shaped to bow into the lower zone.

7. The invention of claim 3 wherein the facets are planar.

8. The invention of claim 3 wherein the facets define edges at their lines of intersection, and wherein the edges are convexly shaped to bow into the lower zone.

9. The invention of claim 3 wherein the facets define edges at their lines of intersection, and wherein the edges are rectilinear.

10. The invention of claim 1 wherein at least some of the internal corners which converge toward the liquid outlet means define an included angle no greater than 60°.

11. A separator for a gas analyzer, said separator comprising:
    means for defining a separation chamber;
    inlet means for introducing a gas/liquid mixture into the separation chamber;
    gas outlet means for removing gas from the separation chamber; and
    liquid outlet means for removing liquid from the separation chamber;
    said separation chamber bounded by a set of lower walls and an upper wall;
    said upper wall being spherically concave and positioned around said gas outlet means;
    said lower walls arranged as an inverted pyramid such that the lower walls converge downwardly to an apex aligned with the liquid outlet means;
    said lower walls defining a plurality of internal corners, at least a portion of which converge toward the apex in order to draw liquid by capillary action toward the liquid outlet means and away from the gas outlet means;
    said upper wall dimensioned to ensure that all internal corners are spaced from the gas outlet means by a distance greater than 0.05 inches, and said separation chamber having a volume less than 1 milliliter.

12. The invention of claim 11 wherein said lower walls intersect one another at edges of the pyramid, and wherein the edges are tangent to the upper spherically concave wall.

13. The invention of claim 11 wherein the inverted pyramid is a three-sided pyramid.

14. The invention of claim 11 wherein the gas outlet means is centered in the upper wall, directly above the liquid outlet means.

15. The invention of claim 11 wherein said lower side walls intersect one another at edges of the pyramid, and wherein the edges merge with the liquid outlet means smoothly.

16. The invention of claim 11 wherein at least some of the internal corners which converge toward the apex define included angles no greater than 60°.

17. A liquid separator for a gas analyzer comprising:
    a container having an upstanding boss on one surface thereof, said boss defining a vacuum port and a liquid separation chamber;
    said liquid separation chamber having a lower portion generally shaped as an inverted pyramid having an apex in fluid communication with an interior volume defined by the container said inverted pyramid defining a plurality of internal corners, a plurality of which converge toward the apex;
    said liquid separation chamber having an upper portion generally shaped as a dome centered over the inverted pyramid such that the dome forms a convex base for the inverted pyramid;
    a gas outlet port formed in the boss to enter the liquid separation chamber through the dome,
    a gas/liquid inlet port formed in the boss to enter the liquid separation chamber through the inverted pyramid;
    said vacuum port being in fluid communication with the interior volume defined by the container;
    said liquid separation chamber having a volume less than 1 milliliter.

18. The invention of claim 17 wherein the gas/liquid inlet port enters the liquid separation chamber through one of the internal corners of the inverted pyramid.

19. The invention of claim 17 wherein the dome is sized to ensure that the separation between the gas outlet port and all of the internal corners is greater than 0.05 inches.

20. The invention of claim 17 wherein the inverted pyramid defines at least three planar faces.

21. The invention of claim 17 wherein the inverted pyramid defines at least three rectilinear edges which converge toward the apex.

22. The invention of claim 17 wherein the inverted pyramid defines at least three faces, and wherein the faces are bowed inwardly, into the liquid separation chamber.

23. The invention of claim 17 wherein the inverted pyramid defines at least three edges which converge toward the apex, and wherein the edges are bowed inwardly, into the liquid separation chamber.

24. The invention of claim 17 wherein the internal corners which converge toward the apex each define an included angle no greater than 60°.

25. The invention of claim 24 wherein the internal corners which converge toward the apex comprise at least eight internal corners.

* * * * *